United States Patent [19]

McClune et al.

[11] Patent Number: 5,366,864

[45] Date of Patent: *Nov. 22, 1994

[54] BUFFERED WASH COMPOSITION, INSOLUBILIZING COMPOSITION, TEST KITS AND METHOD OF USE

[75] Inventors: Gregory J. McClune, Portage, Mich.; Karen L. Findling, Rochester, N.Y.

[73] Assignee: Eastman Kodak Company, Rochester, N.Y.

[*] Notice: The portion of the term of this patent subsequent to Jan. 5, 2010 has been disclaimed.

[21] Appl. No.: 953,905

[22] Filed: Sep. 30, 1992

Related U.S. Application Data

[62] Division of Ser. No. 447,332, Dec. 7, 1989, Pat. No. 5,176,999.

[51] Int. Cl.$^5$ .................. G01N 33/53; G01N 33/547; G01N 33/76
[52] U.S. Cl. ..................... 435/7.5; 435/7.9; 435/28; 435/810; 435/975; 435/967; 436/532
[58] Field of Search .................. 435/7.5, 7.9, 975, 14, 435/28, 810, 967; 422/61, 55, 57; 428/402.2, 403; 436/66, 65, 532; 8/636

[56] References Cited

U.S. PATENT DOCUMENTS

| | | | |
|---|---|---|---|
| 3,008,879 | 11/1961 | Harvill | 435/28 |
| 4,089,747 | 5/1978 | Bruschi | 435/28 |
| 4,260,393 | 4/1981 | Gibson | 436/66 |
| 4,298,685 | 11/1981 | Parikh et al. | 435/7.5 |
| 4,299,916 | 11/1981 | Litman et al. | 435/6 |
| 4,318,984 | 3/1982 | Magers et al. | 435/14 |
| 4,340,669 | 7/1982 | Bauer | 435/14 |
| 4,496,654 | 1/1985 | Katz et al. | 435/7.5 |
| 4,497,899 | 2/1985 | Armstrong et al. | 435/7.36 |
| 4,517,288 | 5/1985 | Giegel et al. | 435/7.94 |
| 4,737,456 | 4/1988 | Weng et al. | 435/7.92 |
| 4,828,983 | 5/1989 | McClune | 435/7.92 |
| 4,870,007 | 9/1989 | Smith-Lewis | 435/28 |
| 5,017,474 | 5/1991 | McClune et al. | 435/7.5 |
| 5,024,935 | 6/1991 | McClune et al. | 435/7.5 |
| 5,071,745 | 12/1991 | Triscott et al. | 435/7.4 |
| 5,176,999 | 1/1993 | McClune et al. | 435/7.92 |

FOREIGN PATENT DOCUMENTS

| | | |
|---|---|---|
| 302715 | 2/1989 | European Pat. Off. . |
| 308236 | 3/1989 | European Pat. Off. . |
| 2074727 | 11/1981 | United Kingdom . |
| 86-04421 | 8/1986 | WIPO . |
| 07718 | 12/1987 | WIPO . |
| 05972 | 6/1989 | WIPO . |

OTHER PUBLICATIONS

White-Stevens et al, Clin. Chem. 28/4:589-595 (1982).
Fucillo et al, "Rapid Viral Diagnosis" in Manual of Clinical Laboratory Immunology, pp. 489-496 (1986).
Leigh B. Bangs, "Uniform Latex Particles", pp. 15 and 23 and 25 (Seradyn Inc. Indianapolis, Ind. Oct. 1984).
Streitwieser et al, *Introduction to Organic Chemistry*, 2nd Ed., Section 10.3 "Physical Properties of Alcohols", pp. 233-237 and Section 10.9 Physical Properties of Ethers, pp. 260-261 (Macmillan Publishing Co., Inc., New York, 1981.

*Primary Examiner*—David Saunders
*Assistant Examiner*—Carol E. Bidwell
*Attorney, Agent, or Firm*—James L. Tucker

[57] ABSTRACT

A buffered aqueous composition is useful simultaneously as a wash solution and a dye-providing composition in specific binding assays involving enzyme-labeled specific binding reagents. The wash composition includes a dye-providing composition, a buffer and an organic solvent having a certain molecular weight and water-solubility. Another useful composition includes a particulate substrate having avidin attached thereto, and a peroxidase reducing agent. Either composition can be provided in a diagnostic test kit, and can be used to detect a specific binding ligand in assays.

15 Claims, No Drawings

BUFFERED WASH COMPOSITION, INSOLUBILIZING COMPOSITION, TEST KITS AND METHOD OF USE

This is a divisional of Application Serial No. 447,332, filed Dec. 7, 1989 now U.S. Pat. No. 5,176,999.

FIELD OF THE INVENTION

This invention relates to a composition which is useful as a wash solution and dye-providing composition simultaneously in specific binding assays. Further, an immobilizing composition is provided. This invention also relates to a diagnostic test kit containing either composition and to methods for determining specific binding ligands.

BACKGROUND OF THE INVENTION

There is a continuous need in medical practice, research and diagnostic procedures for rapid and accurate determinations of biological substances which are present in biological fluids at low concentrations. For example, the presence of hormones, drugs, narcotics, steroids, polypeptides, prostaglandins, proteins, antibodies or infectious organisms in blood, saliva, urine or other biological fluids must be determined in an accurate and rapid manner for suitable diagnosis or treatment.

To provide such determinations, various methods have been devised for isolating and identifying biological substances employing specific binding reactions between the substance to be determined (identified herein as a "ligand"), and receptor molecules specifically reactive with the ligand. Radioisotopes, fluorogens, chromogens, detectable beads and enzymes have been used to detect the resulting complex between ligand and receptor. One common example of specific binding reactions is an immunoassay in which an antigenic substance and specific antibody thereto react to form an immunological complex.

In recent years, the use of enzyme labels has received increased attention for specific binding assays because of various disadvantages associated with radioactive and fluorescent labels. Assays using enzyme labels include what are known in the art as competitive enzyme immunoassays (EIA) and both direct and indirect enzyme linked immunosorbent assays (ELISA). Another type of useful assay is known as an immunometric or "sandwich" assay, as exemplified in U.S. Pat. No. 4,486,530 (issued Dec. 4, 1984 to David et al). In all of these assays, either a receptor for the ligand, or a known quantity of ligand analog is labeled with a enzyme so that ligand-receptor complexes can be distinguished from unlabeled materials. Generally, the complexes are separated from uncomplexed materials using some type of immobilizing technique with or without washing or filtration.

Peroxidase is one enzyme which has been used to advantage as a label in analytical methods. Peroxidase acts on hydrogen peroxide as a substrate and can oxidize various chromogens or dye-providing materials to provide a detectable species at a rate proportional to the amount of peroxidase present. Various dye-providing materials are known in the art, including benzidine and its derivatives, and various leuco dyes.

U.S. Ser. No. 136,166 (filed Dec. 18, 1987 by McClune and Bishop, now U.S. Pat. No. 5,024,935) describes an improved dye-providing composition which is stabilized with certain polymers. The composition includes dye-providing leuco dyes dissolved in methanol which can be converted to detectable dyes in the presence of peroxidase and hydrogen peroxide. While the described assay has found significant usefulness in the art, particularly for pregnancy tests, separate wash and dye-providing solutions and steps are required for effective results. It would be desirable to eliminate steps and solutions in order to make the test more reliable and simple for the user.

SUMMARY OF THE INVENTION

The useful assay described in U.S. Pat. No. 5,024,935 (noted above) is further improved using a buffered aqueous wash composition comprising:
  a. a composition capable of providing a dye in response to an enzyme which is the label on a specific binding reagent,
  b. a buffer, and
  c. a water-soluble organic solvent which has a molecular weight between about 40 and about 100 and is present in an amount of from about 2.5 to about 25 volume %.

Also provided by this invention is a composition for insolubilizing a biotinylated specific binding reagent, the composition comprising a particulate substrate having avidin attached thereto and a reducing agent for peroxidase. This immobilizing composition can be included in a diagnostic test kit, with or without the wash composition described herein.

This invention also provides a diagnostic test kit comprising:
  a. an enzyme-labeled receptor for a specific binding ligand, and
  b. a buffered aqueous wash composition comprising:
    a. a composition capable of providing a dye in response to the enzyme,
    b. a buffer, and
    c. a water-soluble organic solvent which has a molecular weight between about 40 and about 100 and is present in an amount of from about 2.5 to about 25 volume %.

Further, a method for the determination of a specific binding ligand comprises the steps of:
  A. contacting a specimen suspected of containing a predetermined specific binding ligand with an enzyme-labeled receptor for the ligand to form a detectable complex of ligand and receptor,
  B. washing the detectable complex with a buffered aqueous wash composition comprising:
    a. a composition capable of providing a dye in response to the enzyme,
    b. a buffer, and
    c. a water-soluble organic solvent which has a molecular weight between about 40 and about 100 and is present in an amount of from about 2.5 to about 25 volume %, and
  C. detecting the resulting dye as an indication of the presence of the specific binding ligand in the specimen.

The present invention provides an improved composition which provides a dye in the presence of an enzyme-labeled specific binding reagent, and which is also useful as a wash solution in a specific binding assay. This composition can be used to advantage in assays where any enzyme is used as the label, but particularly when peroxidase is used as the label. Because the composition is useful as a wash solution as well as a dye-providing solution, separate solutions and steps are eliminated. Thus, the assay is simplified, assay time is reduced and the likelihood for error is reduced. The composition of this invention can be readily packaged in a diagnostic test kit which has less components than known kits.

The advantages of this invention are provided in a specially formulated wash composition including a dye-providing composition responsive to an enzyme label, buffer and water-soluble organic solvent which has a molecular weight from about 40 to about 100, and which is present in the composition at a volume percent of about 2.5 to about 25.

When peroxidase is used as the preferred enzyme label, it is necessary to include a reducing agent which will inhibit the peroxidative formation of dye while removing excess peroxidase during the wash step. Advantageously, in some embodiments in which a biotinylated receptor is used, an insolubilizing composition includes a particulate substrate to which avidin is attached, and a peroxidase reducing agent.

DETAILED DESCRIPTION OF THE INVENTION

The wash composition of the present invention is useful for providing a dye in the presence of a an enzyme used as a label on a specific binding reagent, such as an antigen, antibody, hapten or drugs. Representative enzymes include peroxidase, glucose oxidase, alkaline phosphatase, glucosidase, urease, β-glucosidase, β-galactosidase and others known to one skilled in the art. Techniques for attaching such enzymes to specific binding reagents are well known. This composition is particularly useful with conjugates of peroxidase and the specific binding reagent, such as a peroxidase-labeled antibody. Preferably, the wash composition of this invention is used in assays which involve specific binding reactions, such as immunoassays, as described in more detail below.

The wash composition of this invention includes a dye-providing composition which, in turn, includes one or more reagents which provide a dye upon interaction of the enzyme with the appropriate substrates. In some instances, the dye-providing composition is a single reactant which both provides a dye and is the needed substrate for the enzyme. In other embodiments, two or more reagents are needed for enzymatic activity and dye formation.

Depending upon the enzyme used, the dye-providing composition will vary in components. A worker of ordinary skill in the art would know what reagents are needed for a given enzyme, and useful amounts. For example, if glucose oxidase is the label, the dye-providing composition can include an aniline and oxidizable compound to provide a dye. For alkaline phosphatase, a suitable reagent includes a phosphate substrate which will directly or indirectly provide a dye.

In the preferred embodiment where the enzyme is peroxidase, any suitable peroxidase-reactive substrate and dye-former can be used, including tetrabenzidine and its derivatives which are well known in the art. Preferably, the composition includes one or more leuco dyes which are capable of providing a dye in the presence of hydrogen peroxide and a peroxidative substance (that is, peroxidase or a substance that acts like peroxidase). The resulting dye is generally detectable in the visible region of the electromagnetic spectrum (generally from about 400 to about 700 nm). Preferably, the dye is detected at from about 500 to about 650 nm.

Imidazole leuco dyes useful herein are either diarylimidazole or triarylimidazole leuco dyes. Many useful compounds are known in the art, including those described in U.S. Pat. No. 4,089,747 (issued May 16, 1978 to Bruschi) and references noted therein, EP-A-0 122 641 (published Oct. 24, 1984) and Japanese Patent Publication 58(1983)-045,557.

The triarylimidazoles having the following general formula are particularly useful:

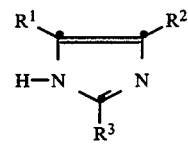

wherein $R^1$, $R^2$ and $R^3$ are each an organic group such that at least one of them is an ortho- or para-hydroxy substituted aryl group of up to 18 carbon atoms, the other two groups being aryl groups chosen such that the imidazole oxidation potential is between about $-70$ and $+110$ mV as measured by cyclic voltammetry against a standard calomel electrode using a carbon based electrode. Oxidation potential measurements can be made according to conventional electrochemical techniques (see, for example, Sawyer et al, *Experimental Electrochemistry for Chemists*, John Wiley & Sons, New York, 1974).

As used herein, the term "aryl" is meant to include aromatic hydrocarbon groups, such as phenyl, naphthyl or anthryl, tolyl, xylyl and other substituted aromatic groups. The number of carbon atoms refers to the total number of nuclear carbon atoms as well as those in substituents. At least one of the $R^1$, $R^2$ and $R^3$ groups has an ortho or para electron donating substituent such as an alkoxy (—OR) wherein R is alkyl of 1 to 8 carbon atoms (for example, methyl, ethyl, isopropyl, t-butyl, hexyl, chloromethyl or methoxymethyl), or a dialkylamino wherein alkyl is as just defined. The $R^1$, $R^2$ and $R^3$ groups can have one or more other substituents which are electronically compatible with the imidazole nucleus to provide a suitable dye upon oxidation. Further details of preferred triarylimidazole compounds and methods of preparing them are found in U.S. Pat. No. 4,089,747 noted above.

Particularly useful triarylimidazole leuco dyes are selected from the group consisting of:
2-(4-hydroxy-3,5-dimethoxyphenyl)-4,5-bis(4-methoxyphenyl)imidazole,
2-(3,5-dibromo-4-hydroxyphenyl)-4,5-diphenylimidazole,
2-(3-bromo-5-methoxy-4-hydroxyphenyl)-4,5-bis(4-methoxyphenyl)imidazole,
4,5-bis(4-dimethylaminophenyl)-2-(4-hydroxyphenyl)imidazole,
4,5-bis(4-dimethylaminophenyl)-2-(4-hydroxy-3-methoxyphenyl)imidazole,
2-(4-hydroxyphenyl)-4,5-bis(4-methoxyphenyl)imidazole, and
4,5-bis(4-dimethylaminophenyl)-2-(4-hydroxy)-3,5-dimethoxyphenylimidazole.

The amount of leuco dye in the preferred wash composition can be varied widely. Generally, it is present in an amount of from about $10^{-6}$ to about $10^{-3}$ and preferably from about $10^{-5}$ to about $10^{-4}$ molar.

The wash composition of this invention is generally buffered to a pH of from about 6 to about 9, depending upon the assay it is being used for. One or more buffers can be used, and suitable buffers are known in the art including, but not limited to phosphates, borates, 3-(N-morpholine)propanesulfonic acid, tris(hydroxymethyl)aminomethane, N-tris-(hydroxymethyl)methyl-2-aminoethane sulfonic acid, N-(2-hydroxyethyl)piperazine-N'-(2-ethanesulfonic) and others readily apparent to one skilled in the art. The amount of buffer can be readily determined to provide the desired pH and buffering capacity. Generally, it is present in an amount of at least about 10 mmolar.

Moreover, the wash composition also includes one or more water-soluble organic solvents having a molecular weight of from about 40 to about 100. Such solvents are polar and have a solubility in water of at least 10% (by volume) at room temperature. Some of the solvents are water-miscible, while others have more limited water-solubility.

Useful solvents must not interfere with the assay in any way, or be detrimental to washing uncomplexed materials or dye formation. A modest experiment may be performed to determine if a particular solvent is useful in the practice of the invention. Particularly useful solvents are the lower alcohols such as ethanol, n-propanol, isopropanol, n-butanol, sec-butanol, tert-butanol and others known to one skilled in the art. Other useful solvents include acetonitrile, ketones such as acetone and methyl ethyl ketone, and ethers such as tetrahydrofuran and 1,4-dioxane. Others would be readily apparent to one skilled in the art. The preferred solvents are the lower alcohols with sec-butanol being most preferred.

The water-miscible solvent is generally present in the composition in an amount of from about 2.5 to about 25, and preferably from about 5 to about 15, volume percent.

In the preferred embodiments wherein the wash composition includes a leuco dye, it also preferably includes one or more water-soluble or water-dispersible polymers, such as vinyl pyrrolidone polymers, acrylamide polymers, acrylic and methacrylic acid polymers, polyethylene glycols and polyamines. These polymers can be either homo- or copolymers. Representative examples of useful polymers include, but are not limited to: poly(acrylic acid), poly(methacrylic acid), poly(acrylic acid-co-methyl acrylate) (90:10 weight ratio), poly(acrylamide), poly(acrylamide-co-acrylic acid) (50:50 weight ratio), polyamines such as those described in U.S. Pat. Nos. 3,702,249 and 4,689,359. Particularly useful polymers are vinyl pyrrolidone polymers, that is a homo- or copolymer prepared from vinylpyrrolidone such as poly(vinylpyrrolidone), poly(vinylpyrrolidone-co-acrylic acid) and poly-(vinylpyrrolidone-co-acrylamide). Further details regarding these polymers are provided in U.S. Pat. No. 5,024,935 (noted above), incorporated herein by reference.

Other optional components of the wash composition include electron transfer agents, such as 4'-hydroxyacetanilide and other phenols as described in U.S. Pat. No. 4,828,983 (issued May 9, 1989 to McClune). Electron transfer agents are compounds which facilitate the transfer of one or more electrons between reactants in oxidation-reduction reactions. Many useful electron transfer agents are known in the art, such as phenazine methosulfate, phenazine ethosulfate, and benzo- and naphthoquinones as described in U.S. Pat. No. 4,746,607 (issued May 24, 1988 to Mura et al).

The components of the wash composition described above are readily available commercially from a number of sources. Alternatively, they can be prepared using known starting materials and procedures, as described in U.S. Pat. No. 4,089,747 and other references noted above.

A preferred wash composition of this invention is buffered to a pH of from about 6 to about 9 and comprises hydrogen peroxide, a phenolic electron transfer agent, poly(vinylpyrrolidone), sec-butanol, and triarylimidazole leuco dye chosen from the list of preferred leuco dyes shown above with 2-(4-hydroxy-3,5-dimethoxyphenyl)-4,5-bis(4-methoxyphenyl)imidazole being most preferred.

A second composition of this invention is used for insolubilizing a biotinylated specific binding reagent or the complex formed from reaction of such reactant with a specific binding partner. For example, this composition can be used to insolubilize the complex formed between an antigen and its corresponding biotinylated antibody. Alternatively, a ternary complex of two antibodies (one being biotinylated) and an antigen can be insolubilized. Further still, a complex of biotinylated antigen, or biotinylated anti-antibody with an antibody to be detected can be insolubilized.

The insolubilizing composition includes a particulate substrate to which avidin is attached in a suitable chemical or mechanical means. Any useful substrate can be used as long as it is particulate, water-insoluble and does not adversely affect the assay. Suitable particulate substrates are regular or irregular in shape and prepared from polymers, glass, ceramics, and other naturally occurring or synthetically prepared materials. Polymeric particles, generally having a diameter from about 0.1 to about 10 $\mu m$, are preferred. The substrate is suspended in an aqueous solution in an amount generally from about 0.1 to about 5 percent solids. One or more buffers can be included within the composition if desired.

Avidin is attached to the substrate using known technology including coating and drying, adsorption and chemical reaction. Generally, it is covalently attached by reacting amino groups on the avidin molecule with activated carboxy, activated haloalkyl, activated chloroethylsulfonyl or other reactive groups on the particles. A preferred procedure is described in U.S. Ser. No. 315,086 (filed Feb. 24, 1989 by Sutton).

A reducing agent is also included in the insolubilizing composition so that any unbound peroxidase will not prematurely oxidize the dye or leuco dye which is responsive to a peroxidative substance. Useful reducing agents, include but are not limited to, ascorbic acid or salts thereof (such as ascorbate), alkali bisulfites (such as sodium bisulfite), water-soluble hydroquinones (such as hydroquinone sulfonic acid) and others readily apparent to one skilled in the art. Ascorbate is preferred. The reducing agent is generally present in an amount of at least about 5 $\mu$molar, and preferably from about 10 $\mu$molar to about 200, mmolar.

The insolubilizing composition preferably includes one or more water-soluble organic solvents having the same properties as those described above for the wash composition. The particular solvents used in the two compositions can be the same or different, in the same or different amounts. Preferably, the solvents used in a given assay are the same.

Both the wash and insolubilizing compositions are prepared by mixing the individual components together in any suitable manner and container. Each can be used immediately, or stored for later use, for example, in a diagnostic test kit.

A diagnostic test kit can include the wash composition described above as well as one or more other components, equipment, instructions and the like needed for a specific binding assay. Particularly, the test kit includes a receptor for the specific binding ligand. Other useful components of the kit include additional receptors (such as a second receptor which is biotinylated), labeled or unlabeled, labeled ligand analogs, the immobilizing composition of this invention, materials which bind specifically to the receptor or ligand, disposable test devices (described below), reagent containers, pipettes, prefilter devices, and other reagents known to one skilled in the art.

Disposable test devices generally comprise a water-insoluble substrate having one or more test zones (such as test wells). The substrate is prepared from a water-insoluble material such as glass, polymeric materials, cellulosic materials and other materials known in the art. The device can be a test tube, petri dish, filter paper or test strip having the zones for reaction. It can also be a microtest plate having a multiplicity of preformed test wells. Particularly useful test devices are described and claimed in U.S. Pat. No. 4,870,007 (issued Sep. 26, 1989 to Smith-Lewis), incorporated herein by reference, which are available commercially in diagnostic test kits identified as Surecell ™ test kits by Eastman Kodak Co.

The present invention provides a method whereby a detectable complex between a ligand (a substance to be detected) and a receptor (a compound which reacts specifically with the ligand) is obtained. Advantageously, the method is simple and therefore can be performed in a doctor's office or in a consumer's home to provide immediate results. The test can be used to detect the presence or absence of a mono- or multivalent or multideterminant ligand in an aqueous liquid, such as a biological fluid.

More specifically, the present invention can be used in the determination (qualitative or quantitative measurement) of a ligand in aqueous liquids to which there are naturally occurring or synthetically produced specific binding receptors. This determination can be made by merely determining the presence or absence of the ligand, or by quantitatively determining the amount of ligand. In particular, the invention can be used to assay biological fluids of animals, humans or plants, but preferably of humans. Such fluids include, but are not limited to, whole blood, plasma, sera, lymph, bile, urine, spinal fluid, seminal fluid, lacrimal fluid, vaginal secretions, sputum, perspiration and the like as well as stool specimens. It is also possible to assay fluid preparations of human or animal tissue such as skeletal muscle, heart, kidney, lungs, brains, bone marrow, skin and the like.

The ligand of interest can be an immunological species which is (1) any substance which, when presented to an immunocompetent host, will result in the production of a specific antibody capable of binding with that substance, or (2) the antibody so produced, which ligand participates in an antigen-antibody reaction.

Representative ligands detectable with the present invention include primary amines, amino acids, peptides, polypeptides, proteins, lipoproteins, glycoproteins, drugs, haptens, enzymes, steroids, lipids, nucleic acids, hormones, vitamins, polysaccharides, glycolipids, alkaloids, organisms (bacteria, protozoa, fungi, viruses including retroviruses, rickettsia and the like) and components thereof, blood components, tissue and organ antigens and other materials known to one skilled in the art. In some instances, the ligand is an antibody which is directed against a drug, hormone, antibiotic or other compound having antigenic properties. Alternatively, the ligand can be an antigenic material. In still another embodiment, the immunological species is an antibody which is directed against another antibody (that is, an anti-antibody). Both monoclonal and polyclonal antibodies can be used, and they can be whole molecules or various fragments thereof. Preferably, monoclonal antibodies are used in the assays.

In a preferred embodiment, the method is useful for the detection of hCG in urine or blood as an early indicator of pregnancy. In this embodiment, one or more different antibodies to hCG are immobilized in the test device in order to provide reagents for forming a complex with hCG at different epitopic sites. This embodiment is described in more detail in U.S. Pat. No. 4,870,007 (noted above).

Generally, the method of this invention is carried out by contacting an enzyme-labeled receptor for a ligand of interest with a sample of liquid suspected of containing the ligand in such a manner as to form a reaction product (that is, complex) of any ligand present and the enzyme-labeled receptor. Generally, the liquid sample is applied to a test zone of a test device or placed in a test well, depending upon the configuration of the device. The presence or absence of the reaction product is then determined in a suitable manner after washing the complex with the wash composition of this invention, separating unreacted materials from the reaction complex. Dye is provided from the composition in the presence of the substrate and dye providing reagents.

The method of the invention can be a competitive binding immunoassay using both enzyme-labeled and unlabeled receptor. Either bound (that is, complexed) or unbound (that is, uncomplexed) materials can be determined. Physical separation of bound and unbound materials, if desired, can be carried out using any suitable separation equipment and the wash composition of this invention.

In another embodiment, a competitive immunoassay uses a receptor for the ligand and a fixed quantity of enzyme-labeled ligand. Complex formed and detected using the wash composition of this invention is inversely proportional to the amount of ligand in the specimen.

In still another embodiment, the receptor is unlabeled, and the ligand-receptor complex is detected using an enzyme-labeled specific binding reagent which specifically binds to the receptor. For example, if the ligand is an antigenic material, and the receptor is an unlabeled antibody, the labeled specific binding reagent could be an anti-antibody.

In any of these embodiments, the detectable complex can be reacted with a specific binding reagent which complexes with either the ligand or receptor therefor, and which is either insoluble or capable of insolubilizing the complex. For example, the reagent can be avidin attached to an insoluble substrate (particulate or not) if either the ligand or receptor is biotinylated.

In a preferred embodiment, the method is what is known in the art as an immunometric assay. The details of such assays are provided in U.S. Pat. No. 4,486,530 (noted above). Such an assay can be used to determine multivalent or multideterminant ligands as described above, that is ligands having two or more epitopic sites for immunological reaction with two or more, same or different, receptor molecules. In the sandwich assay, a second receptor is brought into contact with the ligand either prior to, simultaneously with or subsequent to contact of the ligand with a first receptor. The result is the formation of a complex of the two receptors with the ligand at least one of which is enzyme-labeled. Preferably, a second receptor is biotinylated. The resulting complex is insolubilized using the insolubilizing composition of this invention as the biotinylated receptor and the avidin on the particulate substrate react, and the resulting insolubilized complex can be separated from unreacted material in a suitable manner. The other receptor in the insolubilized complex is detectable from the enzyme.

In a preferred embodiment, a method for the determination of hCG in an aqueous specimen (urine or blood) comprises the steps of:

A. contacting a specimen suspected of containing human chorionic gonadotropin with a first antibody (preferably, biotinylated antibody) to hCG to form an immunological complex, B. simultaneously with or subsequently to step A, contacting the specimen with a second antibody to hCG to form a sandwich complex, the first and second antibodies being reactive at different epitopes, and at least one of the antibodies being labeled with peroxidase, and the other antibody being either insolubilized or capable of becoming so, C. separating uncomplexed materials from the sandwich complex through a filtration membrane, D. contacting the separated sandwich complex with the buffered aqueous wash composition described herein while in the presence of hydrogen peroxide, and E. detecting the resulting dye as an indication of the presence of hCG in the specimen.

This method can be practiced in a doctor's office or at home for early determination of pregnancy by assaying urine samples.

The following examples are representative of the practice of this invention and is not intended to limit the scope of the invention. All percentages are by weight unless otherwise indicated.

Materials

PVP is poly(1-vinyl-2-pyrrolidone) (MW=40,000) which was obtained from GAF Chemical Corp.

Human chorionic gonadotropin was obtained from Calbiochem.

A biotinylated antibody was prepared using monoclonal anti-hCG antibodies purchased from Immuno-Search, Inc. and biotin N-hydroxysuccinimide purchased from Calbiochem-Behring Corp. following the procedure described by Hofmann et al, *J.A.C.S.* 100, p. 3585 (1978).

The peroxidase-labeled antibody was prepared using monoclonal anti-hCG antibodies purchased from Cambridge Medical Diagnostics and horseradish peroxidase purchased from Miles, Inc. following the procedure described by Yositake et al (*Eur. J. Biochem.*, 101, p. 395, 1979).

Succinylated casein was prepared by reacting casein with an equal weight of succinic anhydride for four hours at 25° C., then purifying the product by dialysis.

Other materials used in the examples were obtained from Eastman Kodak Co. or Sigma Chemical Co.

EXAMPLE 1:

Wash Composition

The following composition was prepared and used as a wash in the determination of hCG as described in Example 3 below.

A solution of 2-4-(hydroxy-3,5-dimethoxyphenyl)-4,5-bis(4-methoxyphenyl)imidazole leuco dye (0.2% leuco dye) and polyvinyl pyrrolidone (20%) in water was prepared. A sample of this solution (5 ml) was added to 50 ml of a solution comprising sodium dihydrogen phosphate (20 mmolar, pH 7.2), diethylenetriaminepentaacetic acid chelating agent (20 $\mu$molar), hydrogen peroxide (16 mmolar), 4'-hydroxyacetanilide electron transfer agent (8 mmolar), sec-butanol (15 ml) and water (30 ml). This provides about 15 volume percent of sec-butanol. The final concentration of leuco dye was 0.01% and that of polyvinyl pyrrolidone was 1%.

EXAMPLE 2

Insolubilizing Composition

An insolubilizing composition of this invention was prepared by suspending particles of poly[styrene-co-m & p-(2-chloroethylsulfonylmethyl)styrene] (96:4 molar ratio) (0.6 percent solids) in phosphate buffer (250 $\mu$l, 100 mmolar, pH 7.2). Avidin had been covalently attached to the particles through the reactive 2-chloroethyl groups on the particles. Also included in the composition were ascorbate (25 mmolar) and sec-butanol (2.5 volume percent).

EXAMPLE 3:

Assay for hCG Using a Wash Composition to Provide a Dye

The wash composition of Example 1, and the insolubilizing composition of Example 2 were used in an assay for hCG in the following manner.

A disposable test device like that described in U.S. Pat. No. 4,870,007 (noted above) having a 5 $\mu$m commercially available nylon filter membrane in each of three test wells was used in the assay. Each membrane had been coated with succinylated casein. The biotinylated antibody (3 $\mu$g) to hCG immobilized within polyacrylamide binder (60 $\mu$g) was coated in one of the test wells. 3-(N-morpholine)propanesulfonic acid (pH 7.5) buffer was dried in a separate location in this test well. A second test well containing dried buffer (2 mg) in polyacrylamide binder (60 $\mu$g) was used as a negative control. The third well contained dried hCG (400 mI.U.) in a separate location from a dried coating of biotinylated anti-hCG antibodies (3 $\mu$g) in polyacrylamide binder (60 $\mu$g) and buffer (2 mg), as a positive control.

A urine specimen (about 200 $\mu$l), prefiltered to remove impurities, and containing about 50 mI.U./ml of hCG was added to each well of the test device, followed by addition of peroxidase-labeled anti-hCG antibodies (40 $\mu$l of a $10^{-9}$ molar solution). After a one minute incubation, the insolubilizing composition of Example 2 (40 $\mu$l of a 0.6% dispersion) was added to each well and the fluid was allowed to drain through the membrane of each well.

Uncomplexed materials were washed through the membranes using the wash composition of Example 1 (110 μl per well). After 2 minutes of incubation, the dye formed on the membranes was measured visually to show a positive test for hCG in the specimen.

EXAMPLE 4:

Assay for hCG Using Ascorbate as the Reducing Agent and Acetonitrile as the Water-Soluble Solvent This example illustrates as assay for hCG using a wash composition containing acetonitrile as the water-soluble solvent and ascorbate as the reducing agent.

The disposable test device used was the same as that described in Example 3.

A wash composition was prepared from the following components: leuco dye (0.01% as in Example 1), polyvinyl pyrrolidone (1%), sodium dihydrogen phosphate (100 mmolar, pH 7.2), diethylenetriaminepentaacetic acid (10 μmolar), 4'-hydroxyacetanilide (4 mmolar), hydrogen peroxide (8 mmolar) and acetonitrile (15 volume %).

The insolubilizing composition (prepared like that described in Example 2) contained: avidin-particle composition (0.94% solids), sodium ascorbate (25 mmolar) glucose (18.5 mmolar), catalase (147 units/ml) and glucose oxidase (0.26 units/ml). The last three components keep the ascorbate in reduced form as long as excess oxygen is prevented from entering the solution.

The assay was carried out as described in Example 3 except that 28 μl of the insolubilizing composition and 160 μl of the wash composition were added to the test device wells.

The dye that formed on the membranes of the test device was evaluated visually as showing a positive test for hCG.

EXAMPLE 5

Assay for hCG Using Ascorbate as the Reducing Agent and sec-Butanol as the Water-Soluble Solvent The assay described in Example 4 was repeated except that the insolubilizing composition contained 200 mmolar ascorbate instead of 25 mmolar. The dye that formed on the test device membranes was evaluated visually as showing a positive result for hCG.

EXAMPLE 6

Assay for hCG Using Hydroquinone Sulfonate as the Reducing Agent and sec-Butanol as the Water-Soluble Solvent This example illustrates an assay for hCG using a wash composition as described in Example 4, except that the water-soluble organic solvent used was sec-butanol (15 volume %), The insolubilizing composition, prepared as described in Example 2, contained an avidin-particle composition (0.94% solids) and hydroquinone sulfonate (10 μmolar) as the reducing agent.

The assay showed a positive indication of hCG on the test device membranes.

The invention has been described in detail with particular reference to preferred embodiments thereof, but it will be understood that variations and modifications can be effected within the spirit and scope of the invention.

We claim:

1. A buffered aqueous wash composition consisting essentially of:
   a. a leuco dye capable of providing a dye in response to peroxidase and hydrogen peroxide, which peroxidase is the label on a specific binding reagent,
   b. a buffer,
   c. a water-soluble organic solvent which has a molecular weight between about 40 to about 100 and is present in an amount of from about 2.5 to about 25 volume %,
   d. an electron transfer agent,
   e. a water-soluble or water-dispersible polymer, and
   f. hydrogen peroxide.

2. The wash composition of claim 1 wherein said leuco dye is a triarylimidazole.

3. The wash composition of claim 1 buffered to a pH of from about 6 to about 9.

4. The wash composition of claim 1 wherein said water-soluble solvent is selected from the group consisting of lower alcohols, acetonitrile, ketones and ethers.

5. The wash composition of claim 4 wherein said water-soluble solvent is sec-butanol.

6. A composition for insolubilizing a biotinylated specific binding reagent, said composition comprising a particulate substrate having avidin attached thereto, a water-soluble organic solvent which has a molecular weight between about 40 and about 100 and is present in an amount of from about 2.5 to about 25 volume % and from about 10 micromolar to about 200 millimolar of a reducing agent.

7. The composition of claim 6 wherein said reducing agent is selected from the group consisting of ascorbic acid, a salt thereof, an alkali bisulfite and a water-soluble hydroquinone.

8. The composition of claim 6 wherein said substrate is a polymeric bead having an average diameter from about 0.1 to about 10 μmeter.

9. A diagnostic test kit comprising:
   a. a peroxidase-labeled receptor for a specific binding ligand, and
   b. a buffered aqueous wash composition consisting essentially of:
      i. a leuco dye capable of providing a dye in response to peroxidase and hydrogen peroxide,
      ii. a buffer,
      iii. a water-soluble organic solvent which has a molecular weight between about 40 to about 100 and is present in an amount of from about 2.5 to about 25 volume %,
      iv. an electron transfer agent,
      v. a water-soluble or water-dispersible polymer, and
      vi. hydrogen peroxide.

10. The test kit of claim 9 further comprising a second receptor for said specific binding ligand, which second receptor is biotinylated.

11. The test kit of claim 9 wherein said leuco dye is a triarylimidazole.

12. The test kit of claim 9 wherein said water-soluble solvent is selected from the group consisting of lower alcohols, acetonitrile, ketones and ethers.

13. The test kit of claim 12 wherein said water-soluble solvent is sec-butanol.

14. The test kit of claim 9 wherein said peroxidase-labeled receptor is a peroxidase-labeled antibody to human chorionic gonadotropin, and further comprises:
   a second antibody to human chorionic gonadotropin wherein said antibody is a biotinylated antibody, and
   a composition for insolubilizing said biotinylated antibody comprising polymeric particles having avidin attached thereon, and a reducing agent.

15. The test kit of claim 9 further comprising a composition for insolubilizing a biotinylated specific binding reagent, said composition comprising a particulate substrate having avidin attached thereto and a reducing agent.

* * * * *